(12) United States Patent
Tedeschi et al.

(10) Patent No.: US 6,218,016 B1
(45) Date of Patent: Apr. 17, 2001

(54) LUBRICIOUS, DRUG-ACCOMMODATING COATING

(75) Inventors: Eugene Tedeschi, Santa Rosa, CA (US); Chirag B. Shah, Nashua, NH (US)

(73) Assignee: Medtronic AVE, Inc., Santa Rose, CA (US)

( * ) Notice: Subject to any disclaimer, the term of this patent is extended or adjusted under 35 U.S.C. 154(b) by 0 days.

(21) Appl. No.: 09/405,024

(22) Filed: Sep. 27, 1999

Related U.S. Application Data

(63) Continuation-in-part of application No. 09/163,038, filed on Sep. 29, 1998.

(51) Int. Cl.$^7$ .......................... B32B 27/42; B32B 15/08; B05D 3/02; A61K 31/785
(52) U.S. Cl. .................... 428/423.1; 428/424.2; 428/424.4; 428/457; 428/461; 424/422; 424/405; 424/78.08; 427/385.5; 427/388.1; 427/393.5
(58) Field of Search ............... 428/423.1, 424.2, 428/424.4, 457, 461; 424/422, 405, 78.08; 427/385.5, 388.1, 393.5

(56) References Cited

U.S. PATENT DOCUMENTS

| | | | |
|---|---|---|---|
| 4,373,009 | 2/1983 | Winn | 428/424.2 |
| 4,585,666 | 4/1986 | Lambert | 427/2 |
| 4,625,012 | * 11/1996 | Rizk et al. | 528/28 |
| 5,032,666 | 7/1991 | Hu et al. | 528/70 |
| 5,040,544 | 8/1991 | Lessar et al. | 128/784 |
| 5,134,192 | 7/1992 | Feijen et al. | 525/54.1 |
| 5,405,919 | 4/1995 | Keefer et al. | 525/377 |
| 5,470,307 | 11/1995 | Lindall | 604/20 |
| 5,512,055 | 4/1996 | Domb et al. | 604/265 |
| 5,525,348 | 6/1996 | Whitbourne et al. | 424/423 |
| 5,525,357 | 6/1996 | Keefer et al. | 424/486 |
| 5,605,696 | 2/1997 | Eury et al. | 424/423 |
| 5,612,052 | 3/1997 | Shalaby | 424/426 |
| 5,645,931 | 7/1997 | Fan et al. | 428/334 |
| 5,662,960 | 9/1997 | Hostettler et al. | 427/2.3 |
| 5,674,192 | 10/1997 | Sahatjian et al. | 604/28 |
| 5,676,963 | 10/1997 | Keefer et al. | 424/423 |
| 5,698,738 | 12/1997 | Garfield et al. | 564/112 |
| 5,718,892 | 2/1998 | Keefer et al. | 424/78.27 |
| 5,770,229 | 6/1998 | Tanihara et al. | 424/488 |
| 5,770,645 | 6/1998 | Stamler et al. | 524/419 |
| 5,776,611 | 7/1998 | Elton et al. | 428/423.1 |
| 5,797,887 | 8/1998 | Rosen et al. | 604/265 |
| 5,849,368 | 12/1998 | Hostettler et al. | 427/536 |
| 5,919,570 | 7/1999 | Hostettler et al. | 428/424.8 |

FOREIGN PATENT DOCUMENTS

| | | |
|---|---|---|
| 0 357 401 B1 | 3/1990 | (EP) . |
| 352295 B1 | 6/1993 | (EP) . |
| 397784 B1 | 10/1993 | (EP) . |

* cited by examiner

Primary Examiner—Thurman K. Page
Assistant Examiner—Blessing Fubara
(74) Attorney, Agent, or Firm—Sterne, Kessler, Goldstein & Fox P.L.L.C.

(57) ABSTRACT

A coating is provided for a substrate comprising a polyisocyanate; an amine donor and/or hydroxyl donor; an isocyanatosilane adduct having terminal isocyanate groups and at least one hydrolyzable alkoxy group bonded to silicon; and optionally a polymer selected from the group consisting of polyethylene oxide, polyvinyl pyrrolidone, polyvinyl alcohol, polyethylene glycol, and polyacrylic acid. The coating can accommodate a drug so that when the coating is applied to a medical device, the medical device becomes drug-releasing when in contact with aqueous body fluid. A coated article as well as a method for preparing the coating is also provided.

38 Claims, No Drawings

LUBRICIOUS, DRUG-ACCOMMODATING COATING

This application is a continuation-in-part of U.S. application Ser. No. 09/163,038, filed Sep. 29, 1998, herein incorporated by reference in its entirety.

BACKGROUND OF THE INVENTION

1. Field of the Invention

This invention relates generally to a lubricious, drug-accommodating, coating which may be applied to a substrate in one step. More particularly, the invention relates to a drug-coating complex which is drug-releasing in physiological media. The invention also relates to a method for the production of a lubricious coating and the use thereof as a drug eluting or drug releasing coating.

2. Related Art

It has long been known that hydrophilic coatings with low friction (coefficient of friction of 0.3 or less) are useful for a variety of medical devices such as catheters, catheter introducers and the like. When low friction surfaces are used, the devices, upon introduction into the body, slide easily within arteries, veins and other body orifices and passageways. There have been a wide variety of methods used to provide the surfaces desired. In some cases the material of the catheter or medical device is formed of a material having good anti-friction properties such as poly (tetrafluoroethylene) or other plastics which tend to avoid abrasion with the body. However, in many cases the selection of materials does not provide the anti-slip properties desired in conjunction with other desirable properties for the particular medical device.

Prior art hydrophilic coatings typically rely on a two step, two coating process, usually involving a primer coat of isocyanate or isocyanate/polymer blend which is dried, followed by a second coat containing at least one hydrophilic polymer such as polyvinyl pyrrolidone or polyethylene oxide. The two coatings, one superimposed on the other, are then baked to effect a cure. This forms an interpolymer complex or a network including the hydrophilic polymer. Several disadvantages to this process exist.

First, the exact ratio of primer material to the hydrophilic polymer is difficult to control, as it depends on whatever amounts of primer and hydrophilic polymer happen to be deposited by the wet film during the respective coating steps. Second, the primer may begin to redissolve in the second coating solution, causing some loss of primer and further resulting in difficulty in controlling the primer/hydrophilic polymer ratio. Third, the hydrophilic polymer is not covalently bonded to the substrate and may bond to other materials in the area leading the coating to lose its desired properties. Fourth, additional facilities and time are needed for coating with a two step process, as compared to a one step process.

Prior patents have suggested applying solutions of polyvinylpyrrolidone with isocyanate and/or polyurethane in multi-step operations. These coatings often lack good durability. For example, U.S. Pat. No. 4,585,666 issued to Lambert discloses medical devices having hydrophilic coatings formed from an isocyanate layer overcoated with a polyvinylpyrrolidone layer. However, the multistep procedure makes it difficult to tailor the properties and values of the final coatings.

U.S. Pat. No. 4,625,012, Rizk et al., describes a one step method for preparing moisture curable polyurethane polymers having pendant alkoxysilane groups and isocyanate terminals on a substrate. The method includes reacting an isocyanatosilane adduct and an isocyanate different from the isocyanatosilane with a polyol. The isocyanatosilane adduct and the isocyanate have at least two isocyanato groups each. Furthermore, the isocyanatosilane is produced by reacting an isocyanate having at least three isocyanato groups with an organofunctional alkoxysilane. The coating formed, however, is not lubricious.

In U.S. Pat. No. 4,373,009, Winn, a coating process for preparing a lubricious coating is disclosed. A coupling agent is first applied to the substrate. A coating is then applied on top of the coupling agent. The coupling agent bonds the coating to the substrate. Although the coupling agent and coating may be applied to the substrate from the same solution, the preferred method is to apply them separately.

U.S. Pat. No. 5,645,931, Fan et al., describes a one step coating process for preparing a thromboresistant lubricious coating. The coating is comprised of a substantially homogeneous composite of polyethylene oxide and polyisocyanate in an inert solvent. However, the one step coating process is only suitable for polymeric substrates.

U.S. Pat. No. 5,662,960, Hostettler et al., describes a process for producing slippery, tenaciously adhering hydrogel coatings containing a polyurethane-polyurea (PU/PUR) hydrogel commingled with a poly(N-vinyl pyrolidone) hydrogel. The coating may be applied on plastic, rubber, or metallic substrates. However, the process is performed in several steps. Initially, plastic substrates are activated by oxidative chemical treatments and plasma treatments with oxygen or nitrogen containing plasma gases. Metallic substrates are treated with aminosilane primers. Then, a base coat of PU/PUR hydrogel is applied to the substrate followed by the application of a coat of a second hydrogel.

Exposure to a medical device which is implanted or inserted into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to medical devices include inflammation and cell proliferation which can lead to hyperplasia, occlusion of blood vessels, platelet aggregation, rejection of artificial organs, and calcification.

To counter the adverse reactions which often accompany a medical implant or insert, pharmaceutically-active agents have been applied to or embedded within medical devices by covering the surface with a coating containing the active agent. Accordingly, medical device coatings are known which release a pharmaceutically-active agent via dissolution of the active or by cleavage of the active from the coating. Other drug-releasing coatings operate by hydrolyzing or otherwise cleaving a coating-active agent bond.

One approach to the incorporation of a pharmaceutically active agent into a polymeric network is to absorb the active agent into the coating from a solution. Hydrophilic polymers in contact with an aqueous solution of an active agent, such as by soaking the polymer in a solution of the active agent, will swell to contain the solution and absorb the active agent dissolved therein. Upon drying, the polymeric network includes the associated active agent. The use of such a polymeric network as a coating for a medical device allows for the association and immobilization of a water soluble active agent with and/or within the medical device. The active agent can then be released from the coating upon contact with aqueous body fluids.

Another approach to the association of a pharmaceutically-active agent with a polymeric coating is by chemical attachment, e.g., covalent attachment, of the active agent to the coating. For example, coating compositions are known which include a nitric oxide-releasing functional group bound to a polymer. U.S. Pat. Nos. 5,676,963 and 5,525,357 disclose such polymeric coating compositions.

Nitric oxide (NO), has been implicated in a variety of bioregulatory processes, including normal physiological control of blood pressure, macrophage-induced cytostasis and cytoxicity, and neurotransmission. NO inhibits the aggregation of platelets. NO also reduces smooth muscle proliferation, which is known to reduce restenosis. Consequently, NO can be used to prevent and/or treat complications such as restenosis and thrombus formation when delivered to treatment sites inside an individual that have come in contact with synthetic medical devices.

Nitric oxide appears to play a primary role in the development of an erection and the controllable and predictable release of NO to the penis by a catheter or other delivery means coated with or made of a NO-releasing polymer is described in U.S. Pat. No. 5,910,316.

Because nitric oxide, in its pure form, is a highly reactive gas having limited solubility in aqueous media, it is difficult to introduce in a reliable and controllable form. NO is too reactive to be used without some means of stabilizing the molecule until it reaches the treatment site. Thus, NO is generally delivered to treatment sites in an individual by means of polymers and small molecules which release NO.

The present invention combines the benefits of a lubricious coating with the therapeutic and prophylactic benefits associated with a drug-releasing coating by providing a one step coating which can be made lubricious and/or drug-accommodating and which may be applied in a single step, alleviates the need for a primer or coupling agent, and can be applied on various substrates, including, but not limited to, polymers and metals.

SUMMARY OF THE INVENTION

One aspect of the present invention is directed to a coated substrate comprising (a) a substrate; and (b) a polyurea and/or polyurethane network capable of accommodating a pharmaceutically-active agent, said polyurea and/or polyurethane network formed from the reaction, on at least a portion of the surface of said substrate to be coated, of a mixture comprising a polyisocyanate; an amine donor and/or a hydroxyl donor; an isocyanatosilane adduct having at least one terminal isocyanate group and at least one hydrolyzable alkoxy group bonded to silicon; and optionally a polymer selected from the group consisting of polyethylene oxide, polyvinyl pyrrolidone, polyvinyl alcohol, polyethylene glycol, and polyacrylic acid.

It is a further aspect of the present invention to provide an article comprising a substrate on which a coating is formed comprising a polyurea and/or polyurethane network capable of accommodating a pharmaceutically-active agent, formed from the reaction, on a substrate to be coated, of a mixture comprising a polyisocyanate; an amine donor and/or a hydroxyl donor; an isocyanatosilane adduct having terminal isocyanate groups and at least one hydrolyzable alkoxy group bonded to silicon; and optionally, a polymer selected from the group consisting of polyethylene oxide, polyvinyl pyrrolidone, polyvinyl alcohol, polyethylene glycol, and polyacrylic acid; in a solvent.

It is a further aspect of the present invention to provide a drug-releasing coating comprising an active agent associated with and releaseable from a polymeric network formed from the reaction, on a substrate to be coated, of a mixture comprising a polyisocyanate; an amine donor; and an isocyanatosilane adduct having terminal isocyanate groups and at least one hydrolyzable alkoxy group bonded to silicon; and optionally, a hydroxyl donor and/or a polymer selected from the group consisting of polyethylene oxide, polyvinyl pyrrolidone, polyvinyl alcohol, polyethylene glycol, and polyacrylic acid; in a solvent.

According to yet another aspect of the present invention, a method is provided of preparing a lubricious coating on a substrate to be coated comprising: forming a mixture of a polyisocyanate, an amine donor and/or a hydroxyl donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon, in a solvent; applying the mixture to the substrate; and curing the mixture on the substrate to form the coating.

A further aspect of the present invention is to provide a method of preparing a drug-releasing coating on a substrate to be coated, comprising: forming a mixture of a polyisocyanate, an amine donor, an isocyanatosilane adduct having terminal isocyanate groups and at least one hydrolyzable alkoxy group bonded to silicon, and optionally a hydroxyl donor and/or a polymer selected from the group consisting of polyethylene oxide, polyvinyl pyrrolidone, polyvinyl alcohol, polyethylene glycol, and polyacrylic acid, in a solvent; applying the mixture to the substrate; contacting the coated substrate with a pharmaceutically-active agent; and curing the mixture on the substrate to form the coating.

It is a further aspect of the present invention to provide a drug-releasing coated article or medical device produced by or produceable by the coating method of the present invention.

These and other features and objects of the invention are more fully appreciated from the following detailed description of a preferred embodiment of the invention.

DETAILED DESCRIPTION OF THE PREFERRED EMBODIMENTS

According to the present invention, a lubricious coating is formed by the reaction, on a substrate to be coated, of a mixture comprising a polyisocyanate; an amine donor and/or a hydroxyl donor; an isocyanatosilane adduct having terminal isocyanate groups and at least one hydrolyzable alkoxy group bonded to silicon; and a polymer selected from the group consisting of polyethylene oxide, polyvinyl pyrrolidone, polyvinyl alcohol, polyethylene glycol, and polyacrylic acid; in a solvent. The resulting coating is drug-accommodating and, when the optional hydrophilic polymer is incorporated into the mixture, becomes highly lubricious.

It is believed that the isocyanate functional groups of the polyisocyanate and isocyanatosilane react with the amine donor to form a polyurea network or with the hydroxyl donor to form a polyurethane network. Furthermore, the silane groups of the isocyanatosilane are believed to form covalent bonds with the substrate to which the coating is applied when cured in the presence of moisture to form a strongly adherent coating.

The coating mixture is prepared in solution by weighing the appropriate quantities of polyisocyanate; amine donor and/or hydroxyl donor; isocyanatosilane adduct; and a polymer selected from the group consisting of polyethylene oxide, polyvinyl pyrrolidone, polyvinyl alcohol, polyethylene glycol, and polyacrylic acid; and adding them into an appropriate mixing vessel. Additional solvents may be added to adjust the viscosity of the mixture. The choice of ingredients in the coating mixture also affects the physical properties of the overall coating. Solids contents in a range of from about 0.2 to about 2.5% are preferred. This solution is mixed well and then applied to an appropriate substrate such as catheter tubes, medical tubing introducers, polymer coated medical wires, stents, dilatation balloons, implants, prostheses, and penile inserts, by conventional coating application methods. Such methods include, but are not limited to, dipping, spraying, wiping, painting, solvent swelling, and the like.

The materials of construction of a suitable substrate include, but are not limited to, polymers, metal, glass, ceramics, composites, and multilayer laminates of the aforementioned materials.

The coatings of the present invention are drug-accommodating. As used herein, the term "drug accommodating" refers to the ability of the polymeric network of the coating to associate with a pharmaceutically active agent. The association of the polymeric network of the coating and a pharmaceutically active agent may be accomplished by any mode of molecular recognition or inclusion including, but not limited to, ionic interactions, hydrogen bonding and other dipole-dipole interactions, covalent attachment, interpenetration by solvent swelling, metal ion-ligand interactions, hydrophilic interactions, hydrophobic interactions including $\pi$-$\pi$ stacking interactions, or any combination thereof.

The terms "pharmaceutically active agent", "biologically active compound", "active agent" and "drug" are used herein interchangeably and include pharmacologically active substances that produce a local or systemic effect in an animal. The terms thus means any substance intended for use in the diagnosis, cure, mitigation, treatment or prevention of disease or in the enhancement of desirable physical or mental development and conditions in an animal. The term "animal" used herein is taken to include humans, sheep, horses, cattle, pigs, dogs, cats, rats, mice; birds; reptiles; fish; insects; arachnids; protists (e.g. protozoa); and prokaryotic bacteria.

The active agents that can be delivered according to the present invention include inorganic and organic drugs without limitation and include drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autocoid systems, alimentary and excretory systems, histamine systems, and the like. The active drug that can be delivered for acting on these recipients includes, but is not limited to, anticonvulsants, analgesics, antiparkinsons, antiinflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, and the like.

The present invention is particularly suitable for delivering polypeptide drugs which are water soluble. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; and peptide or polypeptide vaccines. Other particularly suitable drugs include polysaccharide including, but not limited to, hyaluronic acid.

Preferred drugs include anti-thrombogenics, such as heparin and heparin complexes, enoxaprin, aspirin and hirudin; anti-proliferatives, such as monoclonal antibodies capable of blocking smooth muscle cell proliferation, heparin, angiopeptin and enoxaprin; and antioxidants, such as nitric oxide.

Preferred heparin complexes include, but are not limited to, heparin-tridodecylmethylammonium chloride, heparin-benzalkonium chloride, heparin-steralkonium chloride, heparin-poly-N-vinyl-pyrrolidone, heparin-lecithin, heparin-didodecyldimethylammonium bromide, heparin-pyridinium chloride, and heparin-synthetic glycolipid complex.

A preferred embodiment of the present invention involves contacting a medical device having a lubricious, drug-accommodating, coating of the invention with an aqueous solution containing a pharmaceutically active agent dissolved or dispersed therein. A hydrophilic polymer coating, or other cellular polymeric coating, when exposed to a solution of an active agent, such as an aqueous solution of heparin, will swell to contain the solution. Upon drying and/or vacuum removal of the solvent, what is left behind is a coated substrate surface which contains the active agent (e.g., heparin) in an inwardly decreasing concentration gradient of an interpenetrating polymeric network. The resulting coating becomes drug releasing when exposed to, and consequently re-hydrated or at least partially dissolved with, aqueous biological fluids.

Another preferred embodiment of the present invention is directed to contacting a medical device having a drug-accommodating coating of the invention with a pharmaceutically active agent capable of forming a covalent bond with one or more functional groups within the polymeric network, such that the pharmaceutically-active agent becomes bound to the coating. In a most preferred embodiment, the nucleophilic nitrogen atoms of the polyurea network are allowed to react with an organic or inorganic compound to form a covalent bond. The resulting coating-active agent bond preferably cleaves to release the active agent when used on a medical device in an environment which can cleave the bond. For example, for covalent bonds subject to cleavage by hydrolysis, the coating becomes drug-releasing in an aqueous environment. For enzymatically-cleavable bonds, the coating becomes drug-releasing in the presence of a suitable enzyme.

An especially preferred active agent for association or bonding to the drug-accommodating coating of the present invention is nitric oxide (NO). Physical association or bonding of an $N_2O_2$ or $N_2O_2^-$ functional group to the polymeric network may be achieved by covalent attachment of a nucleophilic moiety of the polymeric coating with $N_2O_2$. The nucleophilic residue to which the $N_2O_2$ or $N_2O_2$ group is attached may form part of the polymer itself, i.e., part of the polymer backbone, or attached as pendant groups on the polymer backbone. The manner in which the $N_2O_2$ or $N_2O_2^-$ functional group is associated, part of, or incorporated with or contained within, i.e., "bound," to the polymer is inconsequential to the present invention and all means of association, incorporation and bonding are contemplated herein.

The NO-releasing $N_2O_2$ or $N_2O_2^-$ functional group is preferably a nitric oxide/nucleophile adduct, e.g., the reaction product of nitric oxide and a nucleophile. The nucleophilic residue is preferably that of a primary amine, a secondary amine, a polyamine or derivatives thereof. Most preferably, the nucleophilic adduct is a urea derivative, such as the polyurea network formed by the reaction of the amine donor with the polyisocyanate and/or isocyanatosilane of the coating composition.

The nitric oxide-releasing $N_2O_2$ or $N_2O_2^-$ functional groups that are bound to the polymer generally are capable of releasing nitric oxide in an aqueous environment such as body fluid, i.e., they do not require activation through redox or electron transfer. While the polymer-bound NO-releasing coating compositions of the present invention are capable of releasing NO in an aqueous solution, such a composition preferably releases NO under physiological conditions.

After applying the coating solution to a substrate, the solvent is preferably allowed to evaporate from the coated substrate, such as by exposure to ambient conditions for at least 5 minutes.

The coating is subsequently cured. The cure time, temperature, and humidity vary with the choice of solvent, polyisocyanate; polyol and polyamine; isocyanatosilane adduct; and the composition of the substrate. The curing rate may be increased by the addition of small amounts water to the coating mixture prior to applying the coating to the substrate.

Cure temperatures may range from about 75° F. to about 350° F. Cure times may range from about 2 minutes to about 72 hours, depending upon the solvent, cure temperature and the reactivity of the polyisocyanate, amine donor, and isocyanatosilane adduct. Preferred cure conditions are about 150° F. to about 220° F. for about 20 minutes to about 8 hours. In all cases the cure conditions should be non-deleterious to the underlying substrate.

After the coating is cured, it is preferable to rinse or soak the coating in water to remove any uncomplexed polymers. Generally, a brief rinse of 10–15 seconds is sufficient, however, a longer rinse or soak is acceptable since the coating is cured and forms a stable gel when in contact with water. After rinsing, the coating may be dried either at ambient conditions, or at elevated temperatures or combinations thereof at reduced pressure.

After the coating is formed, the coating can imbibe water from an aqueous solution prior to introduction to the body and can become lubricious. Alternatively, the coating can imbibe water solely from body fluids, even if not exposed to water prior to introduction into the body. Because the coating is a cross-linked system, it adheres well to the substrate even when hydrated. The coating retains its lubricating properties even after subsequent drying and rehydration. If the coating is to be used in a body-related application, such as in catheters, introducer tubes and the like, the materials selected should be compatible with the body and non-toxic to the body. Biocompatible materials include, but are not limited to, polyethylene, polypropylene, polyurethane, naturally occurring polymers, stainless steel and other alloys.

The coating may be applied to various substrates, including, but not limited to, metals, ceramics, polymers, and glass.

The coating may be applied to metal substrates such as the stainless steel used for guide wires, stents, catheters and other devices.

Organic substrates which may be coated with the coatings of this invention include, but are not limited to, polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under various trademarks such as Pebax™ available from Atochem, Inc. of Glen Rock, N.J.; Mylar™ available from E. I. duPont deNemours and Co. of Wilmington, Del.; Texin™ 985A from Bayer Corporation of Pittsburgh, Pa.; Pellethane™ available from Dow Chemical of Midland, Mich.; and Lexan™ available from General Electric Company of Pittsfield, Mass.

The polyisocyanate is preferably an aromatic polyisocyanate. More preferably, the polyisocyanate is an aromatic polyisocyanate based on toluene diisocyanate and is dissolved in propylene glycol monomethyl acetate and xylene. Preferably, the amount of polyisocyanate ranges from about 0.2 to about 10 percent by weight based upon 100% total weight of coating mixture. Particularly preferred polyisocyanates include m-xylylene diisocyanate, m-tetramethylxylylene diisocyanate known as meta-TMXDI available from Cytec Industries, Inc., Stamford, Conn., and the aromatic polyisocyanate known as Desmodur CB 60N available from Bayer Corporation, Pittsburgh, Pa.

Examples of suitable amine donors which may be incorporated in the mixture in addition to or in lieu of a hydroxyl donor include, but are not limited to, $C_1$–$C_{10}$ cycloalkyl, alkyl and alkenyl monoamines such as methylamine, ethylamine, diethylamide, ethylmethylamine, triethylamine, n-propylamine, allylamine, isopropylamine, n-butylamine, n-butylmethylamine, n-amylamine, n-hexylamine, 2-ethylhexylamine, cyclohexylamine, ethylenediamine, polyethyleneamine, 1,4-butanediamine, 1,6-hexanediamine, N-methylcyclohexylamine and alkylene amines such as ethyleneimine. Preferred amine donors include triethylene glycolamine which has the formula $H_2NCH_2CH_2OCH_2CH_2OCH_2CH_2NH_2$ and an approximate molecular weight of about 148 available as Jeffamine™ XTJ-504 from Huntsman Corp., Salt Lake City, Utah; polyetherdiamines such as Jeffamine™ XTJ-500 and XTJ-501 which have a predominantly polyethylene oxide backbone and an approximate molecular weight of 600 and 900, respectively, available from Huntsman Corp., Salt Lake City, Utah; polyethertriamines such as Jeffamine™ T-403 which is a polypropylene oxide-based triamine and has an approximate molecular weight of 440 available from Huntsman Corp., Salt Lake City, Utah; and amine terminated polypropyleneglycols such as Jeffamine™ D-400 and Jeffamine™ D-2000 which have approximate molecular weights of 400 and 2000, respectively. Other amine donors include urethane modified melamine polyols containing amine and hydroxyl groups available as Cylink HPC™ from Lytec Industries, West Patterson, N.J.

The hydroxyl donor is preferably a polyol. Polyols useful in this invention may be any of a large number of polyols reactive with the polyisocyanate and isocyanatosilane to form a polyurethane network. Examples of suitable polyols include, but are not limited to, polyester polyols, polyether polyols, modified polyether polyols, polyester ether polyols, castor oil polyols, and polyacrylate polyols, including Desmophen™ A450, A365, and A160 available from Bayer Corporation, Pittsburgh, Pa. Preferred polyols include castor oil derivatives (triglyceride of 12-hydroxyoleic acid) such as DB oil, Polycin™ 12, Polycin™ 55, and Polycin™ 99F available from CasChem, Inc. of Bayonne, N.J. More preferably, the polyol is polyester based, such as Desmophen™ 1800. Suitable diols include, but are not limited to, poly(ethylene adipates), poly(ethyleneglycol adipates), polycaprolactone diols, and polycaprolactone-polyadipate copolymer diols, poly(ethyleneterephthalate) polyols, polycarbonate diols, polytetramethylene ether glycol, ethyleneoxide adducts of polypropylene triols. Suitable products include Desmophen™ 651A-65, 1300-75 and 800 available from Bayer Corporation of Pittsburgh, Pa., Niax™ E-59 and others available from Union Carbide of Danbury, Conn., Desmophen™ 550DU, 1600U, 1920D, and 1150 available from Bayer Corporation. Many other polyols are available and may be used as known to those skilled in the art.

Coating solutions containing amine donors are typically easier to process, quicker to cure, and form more rigid, lower viscosity coatings than coating solutions containing hydroxyl donor and no amine donor. Coating solutions containing amine donors, however, typically have a shorter pot life and form less flexible coatings than coating solutions containing hydroxyl donors.

Hydroxyl donors in the coating solution cause the formation of polyurethane. In contrast, amine donors in the coating solution cause formation of a polyurea network. A polyurea network may provide better biocompatibility and stability than a polyurethane network since chain cleavage does not occur. Further, polyurea networks typically have better network properties, such as fatigue resistance, than polyurethane networks.

The amount of hydroxyl and amine donor in the coating mixture may be varied to obtain desirable surface properties for the coating. For example, the amine donor may be varied to obtain a desired lubricity. Preferably, the amount of hydroxyl donor ranges from about 0.2 to about 10 percent by weight and the amount of amine donor ranges from about 0.2 to about 10 percent by weight based upon 100% total weight of coating mixture.

Preferably, the polymer selected from the group consisting of polyethylene oxide, polyvinyl pyrrolidone, polyvinyl alcohol, polyethylene glycol, and polyacrylic acid is polyethylene oxide. More preferably, the polymer is polyethylene oxide having a molecular weight of about 300,000, such as Polyox™ available from Union Carbide Corp of South Charleston, W. Va. The polymer preferably has a mean molecular weight of from about 100,000 to about 2,000,000, Preferably, the amount of the polymer ranges from about 0.2 to about 20 percent by weight based upon 100% total weight of coating mixture. Reduction of the concentration of the water soluble polymer in the coating matrix will increase the amine concentration in the polymer, thereby increasing the number of nucleophilic amine sites available for reaction with a pharmaceutically-active agent, e.g., by nitrosylation with $N_2O_2$.

The isocyanatosilane adduct has one or more unreacted isocyanate functional groups. An isocyanatosilane having two or more unreacted isocyanate functional groups may be produced by reacting a silane, such as aminosilane or mercaptosilane, with polyisocyanate. The isocyanatosilane has at least one hydrozable alkoxy bonded to silicon. Preferably, the amount of isocyanatosilane ranges from about 0.1 to about 10 percent by weight based upon 100% total weight of coating mixture.

The solvent should not react with the polyisocyanate; amine donor; hydroxy donor; polymer selected from the group consisting of polyethylene oxide, polyvinyl pyrrolidone, polyvinyl alcohol, polyethylene glycol, and polyacrylic acid; or isocyanatosilane adduct but is a solvent for all the components of the mixture. The solvent is preferably free of reactive amine, hydroxyl and carboxyl groups. Suitable solvents include, but are not limited to, methylene chloride, tetrahydrofuran (THF), acetonitrile, chloroform, dichloroethane, dichloroethylene, and methylene bromide. Preferably, the solvent is acetonitrile and THF, especially with a ratio of acetonitrile to THF of about 3:1.

Wetting agents may be added to the coating solution to improve wettability to hydrophobic surfaces. Wetting agents include, but are not limited to, fluorinated alkyl esters, such as Fluorad™ FC-430 available from 3M Corp., and octylphenol ethylene oxide condensates, such as Triton™ X-100 available from Union Carbide. A preferred concentration of wetting agent in the coating solution is from about 0.01 to about 0.2% by weight based upon 100% solids in the coating solution.

Viscosity and flow control agents may be added to the coating mixture to adjust the viscosity and thixotropy of the mixture to a desired level. Preferably, the viscosity is such that the coating may be formed on the substrate at the desired thickness. Viscosities of from about 50 cps to about 500 cps may be used although higher or lower viscosities may be useful in certain instances. Viscosity control agents include, but are not limited to, fumed silica, cellulose acetate butyrate, and ethyl acrylate/2-ethyl hexyl acrylate copolymer. Flow control agents are preferably present in amounts of from about 0.05 to about 5 percent by weight based upon 100% total weight of coating mixture.

Antioxidants may be added to the coating mixture to improve oxidative stability of the cured coatings. Antioxidants include, but are not limited to, tris(3,5-di-t-butyl-4-hydroxybenzyl)isocyanurate, 2,2'-methylenebis(4-methyl-6-t-butylphenol), 1,3,5-trimethyl-2,4,6-tris(3,5-di-t-butyl-4-hydroxybenzyl)benzene, butylhydroxytoluene, octadecyl 3,5-di-t-butyl-4-hydroxyhydrocinnamate, 4,4 methylenebis (2,6-di-butylphenol), p,p'-dioctyl diphenylamine, and 1,1,3-tris-(2-methyl-4-hydroxy-5-t-butylphenyl)butane. Antioxidants are preferably present in amounts from 0.01 to 1 percent by weight based upon 100% total weight of coating mixture.

Conventional pigments may be added to the coating mixture to impart color or radiopacity, or to improve the appearance of the coatings.

Air release agents or defoamers which are optionally included in the coating solution include, but are not limited to, polydimethyl siloxanes, 2,4,7,9-tetramethyl-5-decyn-4,7-diol, 2-ethylhexyl alcohol, and n-beta-aminoethylgamma-amino-propyl-trimethoxysilane. Air release agents are preferably added in amounts from 0.005 to 0.5 percent by weight based upon 100% total weight of coating mixture.

The following non-limiting example is meant to be an illustrative embodiment of the present invention.

EXAMPLE 1

A coating solution was prepared by combining the following ingredients and mixing them thoroughly:
(a) 0.32 g. of an aromatic polyisocyanate adduct based on toluene diisocyanate and dissolved in propylene glycol monomethyl acetate and xylene having an NCO content of about 10.5% and a molecular weight of about 400 available as Desmodur™ CB 60 from Bayer Corporation;
(b) 0.67 g. of a solvent-free, saturated polyester resin (polyol) available as Desmophen™ 1800 from Bayer Corporation;
(c) 0.91 g. of polyethylene oxide available as Polyox™ having a molecular weight of about 300,000 from Union Carbide Corp.,
(d) 76.97 g. acetonitrile;
(e) 21.82 g. THF; and
(f) 2.02 g. 3-isocyanyopropyltriethoxysilane available as UCTI7840-KG from United Chemical Technologies, Bristol, Pa.

Five 18" inch wires were coated with the solution by dipping for 11 seconds. The solvent was evaporated at ambient conditions for approximately 20 minutes. The wires were then placed in an oven at 40° C. for 10 hours to cure the coating.

Upon removal from the oven, the wires were rinsed in water and dried.

The coating was tested by ASTM D 1894-87 Standard Test Methods for Static and Kinetic Coefficients of Friction of Plastic Film and Sheeting.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A drug-releasing coating, comprising:
   at least one drug associated with and releasable from a polyurea network formed from the reaction on a substrate to be coated of a mixture comprising:
   (a) a polyisocyanate;
   (b) an amine;
   (c) an isocyanatosilane adduct having at least one terminal isocyanate group and at least one hydrolyzable alkoxy group bonded to silicon; and optionally
   (d) a polymer selected from the group consisting of polyethylene oxide, polyvinyl pyrrolidone, polyvinyl alcohol, polyethylene glycol, and polyacrylic acid.

2. The drug-releasing coating according to claim 1, wherein said polyisocyanate is an aromatic polyisocyanate based on toluene diisocyanate.

3. The drug-releasing coating according to claim 1, wherein said polymer has a mean molecular weight from about 100,000 to about 2,000,000.

4. The drug-releasing coating according to claim 1, wherein said polymer is polyethylene oxide.

5. The drug-releasing coating according to claim 4, wherein said polyethylene oxide has a molecular weight of about 300,000.

6. The drug-releasing coating according to claim 1, wherein said isocyanatosilane adduct is 3-isocyanatopropyltriethoxysilane.

7. The drug-releasing coating according to claim 1, wherein said reaction is carried out in a solvent selected from tetrahydrofuran, acetonitrile, or methylene chloride.

8. The drug-releasing coating according to claim 1, wherein said solvent is tetrahydrofuran or acetonitrile.

9. The drug-releasing coating according to claim 1, wherein said mixture comprises:
   (a) from about 0.2 to about 10 percent by weight polyisocyanate;
   (b) from about 0.2 to about 10 percent by weight amine donor;
   (c) from about 0.2 to about 20 percent by weight of said polymer; and
   (d) from about 0.1 to about 10 percent by weight isocyanatosilane adduct having at least one terminal isocyanate group and at least one hydrolyzable alkoxy group bonded to silicon.

10. The drug-releasing coating according to claim 1, wherein said amine donor is a polyetherdiamine, a polyethertriamine, a urethane modified melamine polyol or an amine terminated polypropyleneglycol.

11. The drug-releasing coating of claim 1, wherein said drug is associated with said polyurea network by ionic interactions, hydrogen bonding, covalent bonding, metal ion-ligand interactions, hydrophilic interactions, hydrophobic interactions, or any combination thereof.

12. The drug releasing coating of claim 1, wherein said drug is a polypeptide.

13. The drug releasing coating of claim 1, wherein said drug is nitric oxide.

14. The drug-releasing coating according to claim 13, wherein said nitric oxide is associated with said polyurea network as a functional group selected from $N_2O_2$ or $N_2O_2^-$.

15. The drug-releasing coating according to claim 14, wherein said nitric oxide-releasing functional group is covalently attached to said polyurea network.

16. The drug-releasing coating according to claim 15, wherein said nitric oxide-releasing functional group is covalently attached to a nitrogen atom.

17. The drug-releasing coating according to claim 16, wherein said covalent bond comprises $X-N_2O_2$ or $X-N_2O_2^-$, wherein X is a primary amine, a secondary amine, a polyamine or a derivative thereof.

18. An article, comprising (1) a substrate on which is coated (2) a drug-releasing coating, comprising:
   at least one drug associated with and releasable from a polyurea network formed from reaction on a substrate to be coated of a mixture comprising:
   (a) a polyisocyanate;
   (b) an amine donor;
   (c) an isocyanatosilane adduct having at least one terminal isocyanate group and at least one hydrolyzable alkoxy group bonded to silicon; and optionally
   (b) a polymer selected from the group consisting of a polyethylene oxide, polyvinyl pyrrolidone, polyvinyl alcohol, polyethylene glycol, and polyacrylic acid.

19. The article according to claim 18 wherein said substrate is selected from the group consisting of plastic and metal.

20. The article according to claim 18, wherein said polyisocyanate is an aromatic polyisocyanate based on toluene diisocyanate.

21. An article according to claim 18, wherein said isocyanatosilane adduct is 3-isocyanatopropyltriethoxysilane.

22. The article according to claim 18, wherein said reaction is carried out in a solvent selected from tetrahydrofuran, acetonitrile or methylene chloride.

23. The article according to claim 22, wherein said solvent is tetrahydrofuran or acetonitrile.

24. The article according to claim 18, wherein said polymer is polyethylene oxide.

25. The article according to claim 24, wherein said polyethylene oxide has a molecular weight of about 300,000.

26. The article of claim 18, which is a catheter tube, a medical tube introducer, a medical wire, a stent, a dilitation balloon, an implant, a prosthesis or a penile insert.

27. A method of preparing a drug-releasing coating on a substrate to be coated comprising:
 (a) forming a mixture of a polyisocyanate; an amine; an isocyanatosilane adduct having at least one terminal isocyanate group and at least one hydrolyzable alkoxy group bonded to silicon; and optionally a polymer selected from the group consisting of polyethylene oxide, polyvinyl pyrrolidone, polyvinyl alcohol, polyethylene glycol, and polyacrylic acid, in a solvent;
 (b) applying said mixture to said substrate;
 (c) associating a drug with said mixture-applied substrate by contacting said mixture-applied substrate with a drug; and
 (d) curing said mixture on said substrate to form said coating.

28. The method according to claim 27, wherein said mixture is cured on said substrate prior to associating said drug with said mixture-applied substrate.

29. The method according to claim 27, wherein said polymer is polyethylene oxide.

30. The method according to claim 27, wherein said drug is associated with said mixture-applied substrate by contacting said mixture-applied substrate with a solution comprising said drug.

31. The method according to claim 27, wherein said drug is associated with said mixture-applied substrate by contacting said mixture-applied substrate with a gaseous atmosphere comprising said drug.

32. The method according to claim 27, wherein contacting said mixture-applied substrate with said drug results in a covalent bond between said mixture and said drug.

33. The method according to claim 27, wherein contacting said mixture-applied substrate with said drug results in penetration of said drug into said mixture.

34. A drug-releasing coated article produced by the method of claim 27.

35. A drug-releasing coated article comprising:
 at least one drug associated with and releasable from a polyurea network formed from the reaction on a substrate to be coated of a mixture comprising:
 (a) a polyisocyanate;
 (b) an amine donor;
 (c) an isocyanatosilane adduct having terminal isocyanate groups and at least one hydrolyzable alkoxy group bonded to silicon; and optionally; and
 (d) a polymer selected from the group consisting of polyethylene oxide, polyvinyl pyrrolidone, polyvinyl alcohol, polyethylene glycol, and polyacrylic acid;
produceable by the method of claim 27.

36. The drug releasing coating of claim 27, wherein said polypeptide is derived from heparin.

37. The drug releasing coating of claim 1, wherein said polypeptide is derived from a complex selected from the group consisting of heparin-tridodecylmethylammonium chloride, heparin-benzalkonium chloride, heparin-steralkonium chloride, heparin-poly-N-vinyl-pyrrolidone, heparin-lecithin, heparin-didodecyldimethylammonium bromide, heparin-pyridinium chloride, and heparin-synthetic glycolipid complex.

38. In a medical device having a drug-releasing coating, the improvement comprising: a drug-releasing functional group associated with and releaseable from a polyurea network formed by the reaction of a mixture comprising:
 (a) a polyisocyanate;
 (b) an amine; and
 (c) an isocyanatosilane adduct having terminal isocyanate groups and at least one hydrolyzable alkoxy group bonded to silicon; and optionally
 (d) a polymer selected from the group consisting of polyethylene oxide, polyvinyl pyrrolidone, polyvinyl alcohol, polyethylene glycol, and polyacrylic acid.

* * * * *